(12) United States Patent
Grieshaber et al.

(10) Patent No.: US 6,375,642 B1
(45) Date of Patent: Apr. 23, 2002

(54) METHOD OF AND DEVICE FOR IMPROVING A DRAINAGE OF AQUEOUS HUMOR WITHIN THE EYE

(75) Inventors: Hans R. Grieshaber, Schaffhausen (CH); M. D. Robert Stegmann, Pretoria (ZA)

(73) Assignee: Grieshaber & Co. AG Schaffhausen, Schaffenhausen (CH)

( * ) Notice: Subject to any disclaimer, the term of this patent is extended or adjusted under 35 U.S.C. 154(b) by 0 days.

(21) Appl. No.: 09/503,884

(22) Filed: Feb. 15, 2000

(51) Int. Cl.$^7$ ............................................. A61M 35/00
(52) U.S. Cl. ....................................... 604/294
(58) Field of Search ........................ 604/8, 9, 10, 265, 604/266, 294, 48, 51, 54; 623/4.1, 4, 5.11, 5.12

(56) References Cited

U.S. PATENT DOCUMENTS

| | | | |
|---|---|---|---|
| 5,360,399 A | | 11/1994 | Stegmann |
| 5,486,165 A | * | 1/1996 | Stegman ........................ 604/8 |
| 5,626,558 A | * | 5/1997 | Suson ............................ 604/8 |
| 6,142,990 A | * | 11/2000 | Burk ............................. 606/6 |

* cited by examiner

Primary Examiner—Manuel Mendez
(74) Attorney, Agent, or Firm—Henry M. Feiereisen

(57) ABSTRACT

A method for improving a drainage of aqueous humor in an eye of a living being and a device for maintaining the drainage of aqueous humor are described, wherein a first incision is made in a lamellar section of the sclera to form a first scleral flap which is then folded upwards in the direction of the cornea, thereby creating a recess in the sclera. A second scleral flap is formed by incising a second lamellar section in the area of the recess and lifted upwardly in the direction of the first sclera flap, thereby creating a second recess and exposing a portion of the Schlemm's canal for permitting injection of a highly viscous medium. At least one support element is implanted in the lumen of the Schlemm's canal on each of both sides of the second recess and, optionally, in the exposed portion of the Schlemm's canal, whereby each of the support elements is made of a material that is decomposable by the tissue of the Schlemm's canal and/or aqueous humor. For formation of a gap-like opening, the second scleral flap or a portion thereof is detached from the partially aqueous humor-permeable Descemet's membrane in the area of the Schwalbe's line, and the detached portion is held open by several protrusions formed on the support element implanted in the exposed portion of the Schlemm's canal.

20 Claims, 8 Drawing Sheets

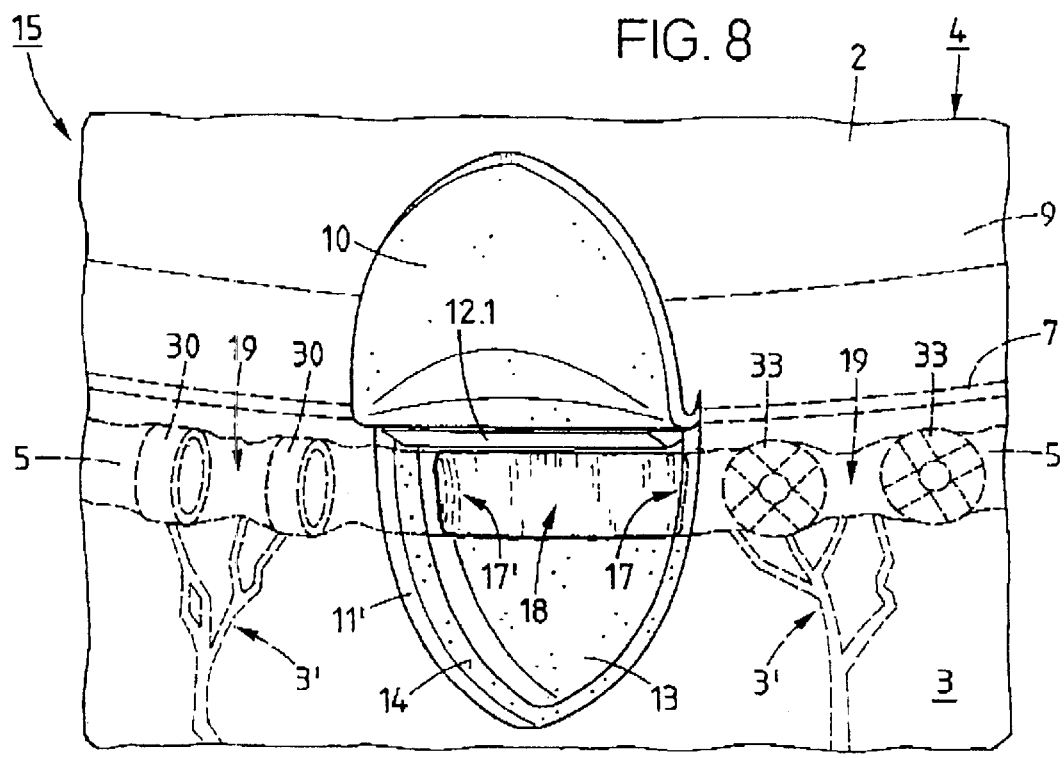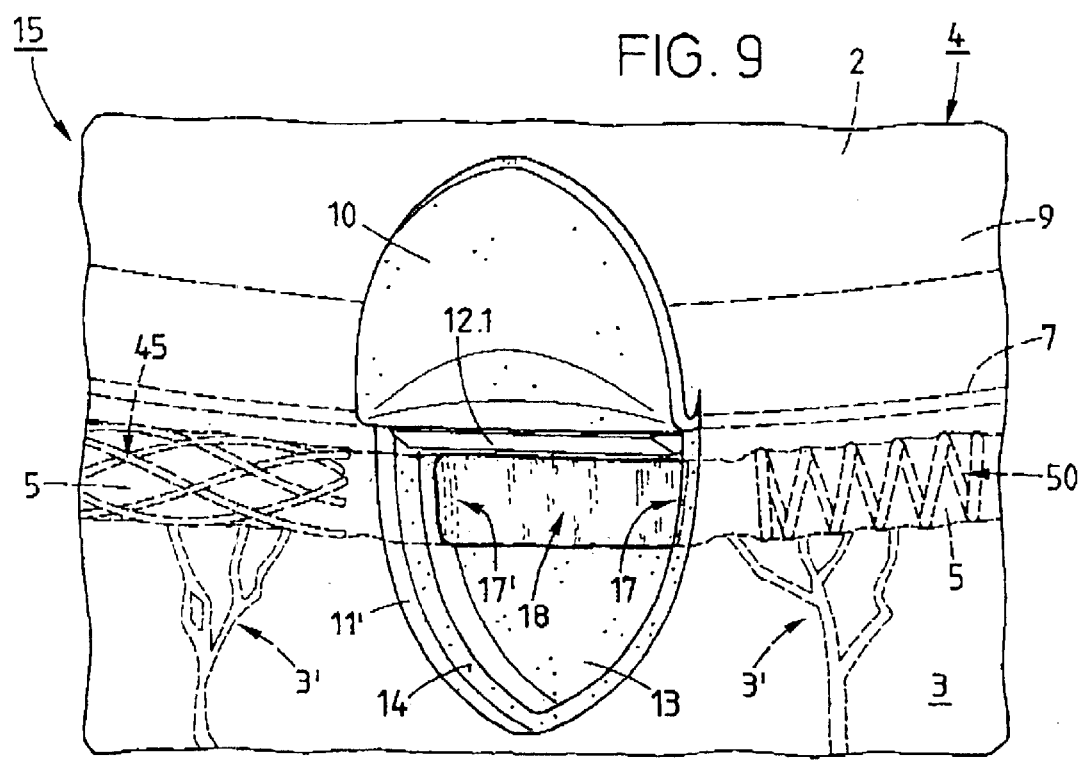

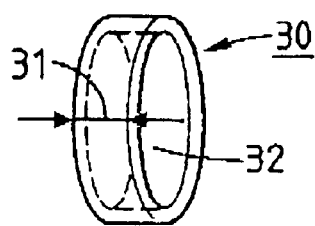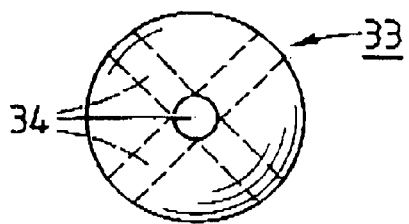
FIG. 10A　　　　FIG. 10B
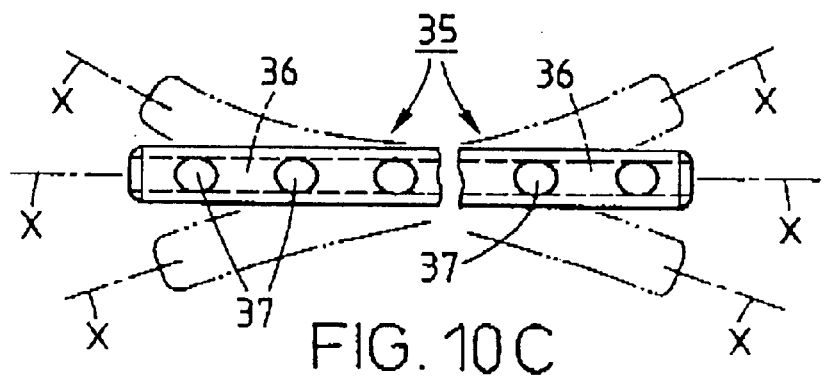
FIG. 10C
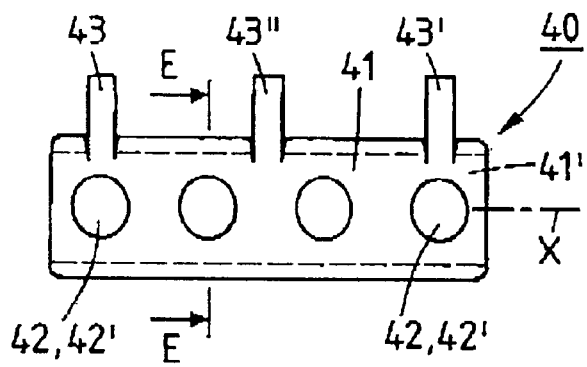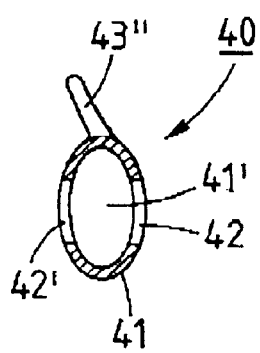
FIG. 10D　　　　FIG. 10E
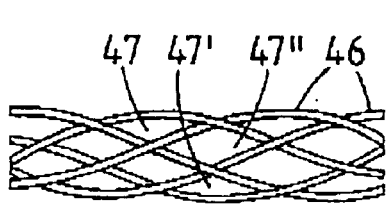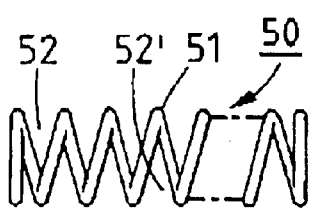
FIG. 10F　　　　FIG. 10G

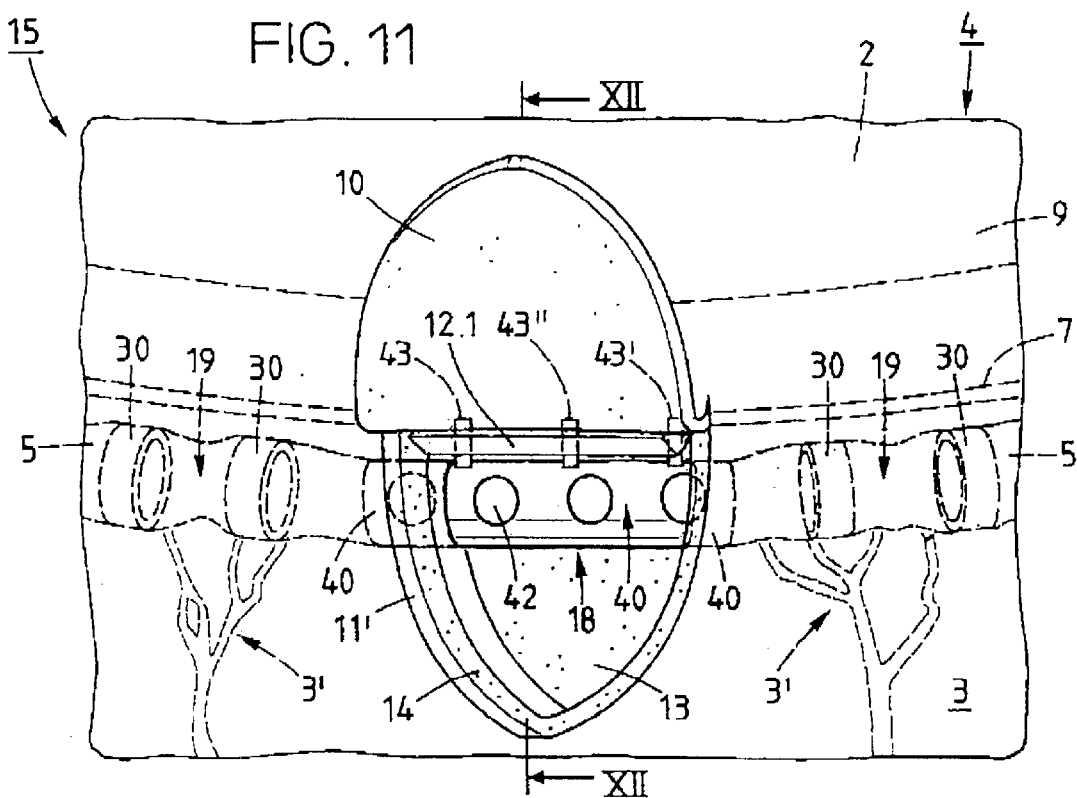
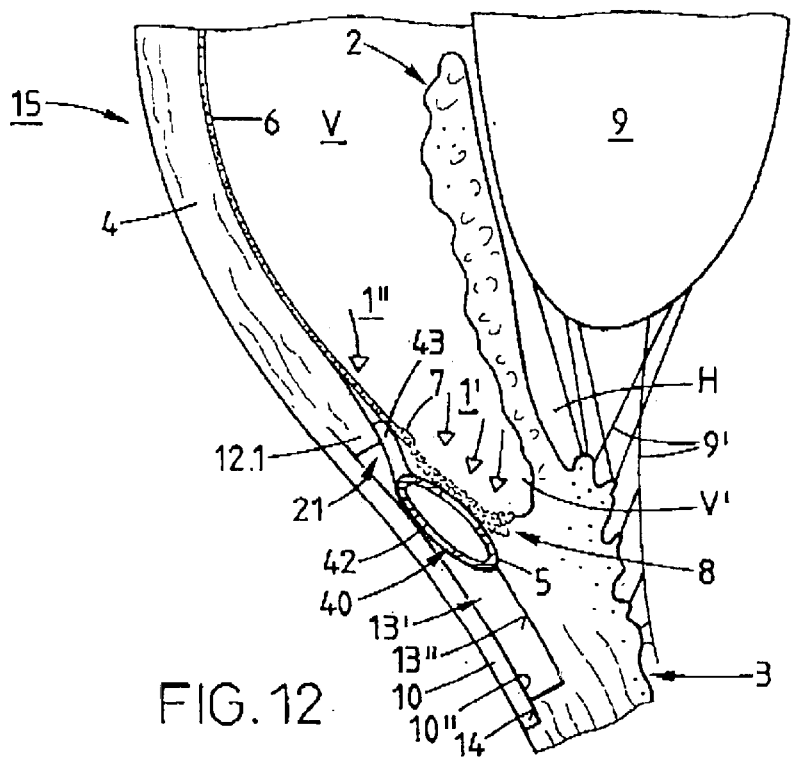

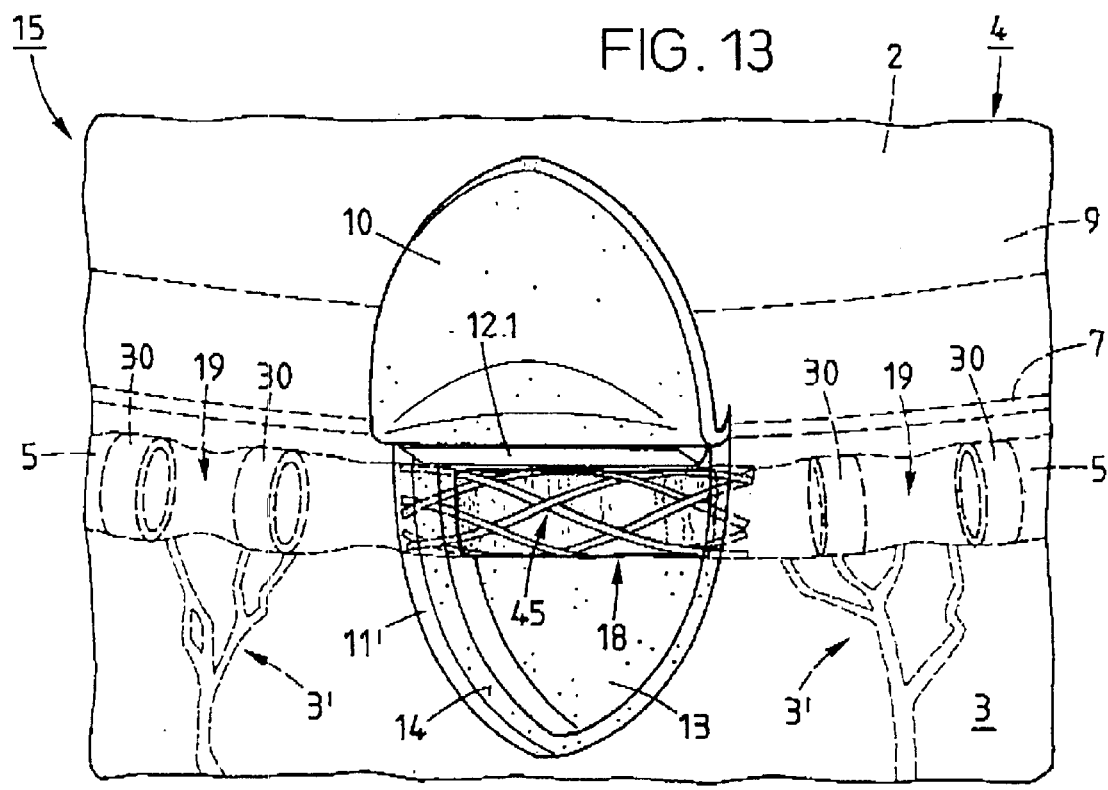
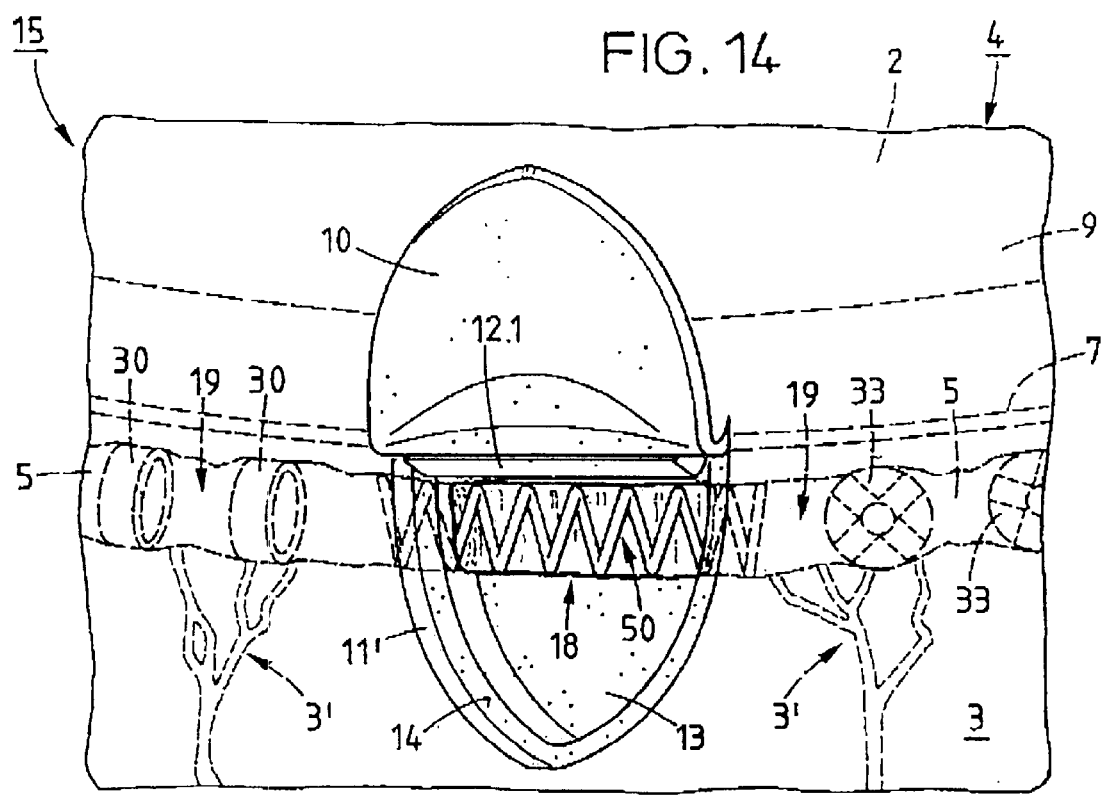

METHOD OF AND DEVICE FOR IMPROVING A DRAINAGE OF AQUEOUS HUMOR WITHIN THE EYE

BACKGROUND OF THE INVENTION

The present invention relates, in general, to a method for improving a drainage of aqueous humor within the eye of a living being, and to a device for maintaining the improved drainage of aqueous humor.

If the trabecular meshwork is either partially or completely non-functional due to an obstruction or back-up, or pathological changes, natural flow of the aqueous humor becomes limited, thereby raising the pressure inside the eye which negatively impacts on the blood circulation and the function of the visual nerve. The resulting disease is commonly known under the name "glaucoma" which may lead to blindness in the eye.

U.S. Pat. No. 5,360,399 describes a method and apparatus, by which the trabecular meshwork, which is located upstream of the Schlemm's canal and which due to pathological changes, may either partially or completely obstruct the outflow of aqueous humor, is slightly widened by the hydraulic pressure of a highly viscous aqueous solution, which when injected into the Schlemm's canal opens it at several location points, so that an outflow of the aqueous humor can be realized.

SUMMARY OF THE INVENTION

It is thus an object of the present invention to provide an improved method for realizing an enhanced flow of aqueous humor within the eye, obviating the afore-stated drawbacks.

In particular, it is an object of the present invention to provide an improved method by which the necessary drainage of the aqueous humor via the outflow pathways of the eye is realized and which thereby results in an improved circulation of the aqueous humor in the eye for regulating the pressure within the eye.

These objects, and others which will become apparent hereinafter, are attained by a method in accordance with the present invention which includes the following steps: incising a first lamellar section of the sclera to form a first scleral flap; lifting the first scleral flap upwards in the direction of the cornea, thereby creating a recess in the sclera; incising a second lamellar section in the area of the recess to thereby form a second scleral flap and a support surface bounding the scleral flap; lifting the second scleral flap upwards in the direction of the first sclera flap, thereby creating a second recess and exposing a portion of the Schlemm's canal; implanting in the lumen of the Schlemm's canal on each of both sides of the second recess, and, optionally, in the exposed portion of the Schlemm's canal, at least one support element, with each support element being made of a material that is decomposable by the tissue of the Schlemm's canal and/or the aqueous humor; folding the first scleral flap back, after severance of the second scleral flap, for placement upon the support surface, thereby confining a subscleral space adjacent the first scleral flap; injecting a viscous medium into the subscleral space; and rejoining the first scleral flap to the sclera.

According to another feature of the present invention, the support element is suitably made of biolytically decomposable material and may have a ring-shaped or spherically-shaped configuration or may have an elongate, tubular configuration to hold the lumen in expanded position. The support element may also be formed as a braided mesh of elongate configuration, or as an elongate helical spring.

In accordance with a further feature of the present invention, the second scleral flap can be detached along a portion thereof in the area of the Schwalbe's line from the partially aqueous humor permeable Descemet's membrane by applying a slight pressure force to thereby form a gap-shaped opening (window). The detached portion of the second scleral flap can thereby be held in open disposition by protrusions projecting out from the support element, so that the anterior chamber is fluidly connected in the area of the iridocorneal angle via the Descemet's membrane and the gap-shaped opening with the subscleral space. In this manner, aqueous humor flowing naturally via the trabecular meshwork into the Schlemm's canal is additionally conducted from the anterior chamber through the partially aqueous humor-permeable Descemet's membrane and through the gap-shaped opening into the scleral space in fluid communication with the Schlemm's canal.

It is another object of the present invention to provide an improved device for realizing and maintaining an enhanced flow of aqueous humor within the eye.

This object is attained in accordance with the present invention by providing a support element for implantation into the lumen of the Schlemm's canal, with the support element having a ring shaped configuration, spherical shaped configuration or tubular shaped configuration, and being made of a decomposable material, in particular of a material that can be decomposed by the tissue of the Schlemm's canal and/or the aqueous humor.

BRIEF DESCRIPTION OF THE DRAWING

The above and other objects, features and advantages of the present invention will be more readily apparent upon reading the following description of a preferred exemplified embodiment of the invention with reference to the accompanying drawing, in which:

FIG. 8 is a schematic view of the portion of the eye of FIG. 4, illustrating exemplified support elements according to the present invention for implantation in the lumen of the Schlemm's canal;

FIG. 9 is a schematic view of the portion of the eye of FIG. 4, illustrating further exemplified support elements according to the present invention for implantation in the lumen of the Schlemm's canal;

FIG. 10A is a detailed perspective view, on an enlarged scale, of a first variation of a support element according to the present invention;

FIG. 10B is a detailed perspective view, on an enlarged scale, of a second variation of a support element according to the present invention;

FIG. 10C is a detailed view, on an enlarged scale, of a third variation of a support element according to the present invention;

FIG. 10D is a detailed view, on an enlarged scale, of a fourth variation of a support element according to the present invention, for exemplified implantation in the exposed portion of the Schlemm's canal;

FIG. 10E is a detailed view, on an enlarged scale, of the support element of FIG. 10D, taken along the line E—E in FIG. 10D;

FIG. 10F is a detailed view, on an enlarged scale, of a fifth variation of a support element according to the present invention;

FIG. 10G is a detailed view, on an enlarged scale, of a sixth variation of a support element according to the present invention;

FIG. 11 is a schematic view of the portion of the eye of FIG. 8, illustrating the exemplified implantation of support elements of FIG. 10A in the Schlemm's canal and the exemplified implantation of support elements of FIG. 10B in the exposed portion of the Schlemm's canal;

FIG. 12 is a schematic view of the portion of the eye of FIG. 11, taken along the line XII—XII in FIG. 11, illustrating the exemplified implantation of a support element of FIG. 10E and folding back of the first scleral flap;

FIG. 13 is a schematic view of the portion of the eye of FIG. 8, illustrating the exemplified implantation of support elements of FIG. 10A in the Schlemm's canal and the exemplified implantation of a support element of FIG. 10F in the exposed portion of the Schlemm's canal; and FIG. 14 is a schematic view of the portion of the eye of FIG. 8, illustrating the exemplified implantation of support elements of FIG. 10A and FIG. 10B in the Schlemm's canal and the exemplified implantation of a support element of FIG. 10G in the exposed portion of the Schlemm's canal.

DETAILED DESCRIPTION OF PREFERRED EMBODIMENTS

Figure 1:
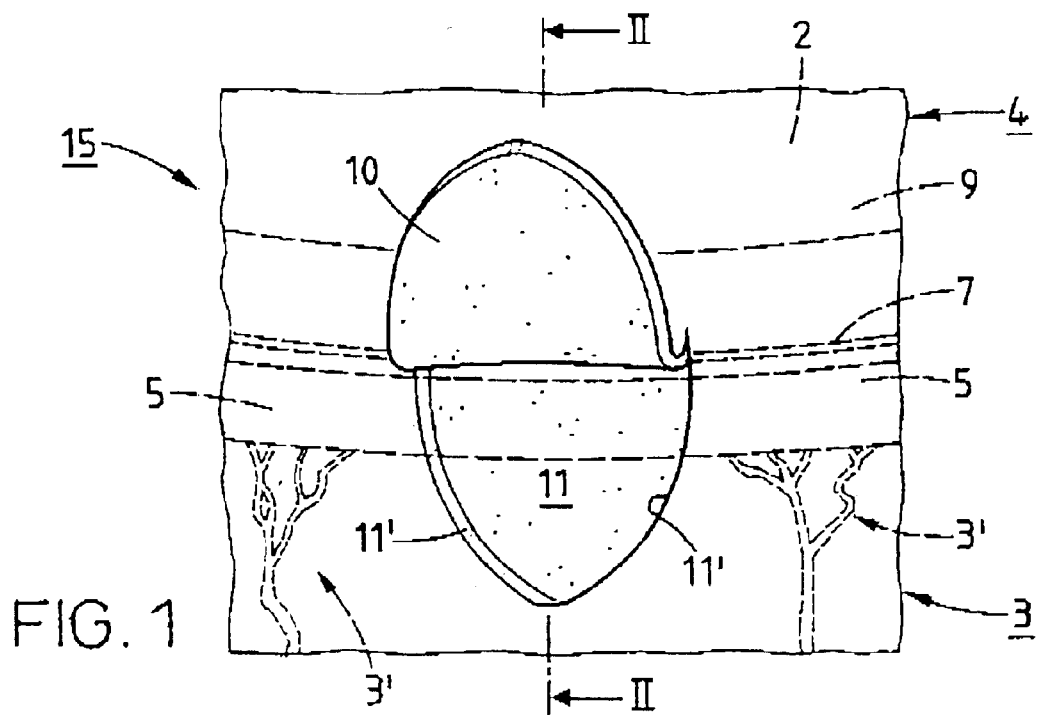
FIG. 1 is a schematic illustration of a portion of a eye, on an enlarged scale, showing a first parabolic incision in the sclera for forming a first scleral flap which is folded upwards.

Turning now to the drawing, and in particular to FIG. 1, there is shown a first process step for improving a drainage of aqueous humor in an eye 15 which is shown only schematically by way of a portion of an iris 2, a cornea 4, a sclera 3, a partial section of the circular Schlemm's canal 5 (sinus venosus sclerae) and a channel system 3' which is comprised of a multitude of channels for conducting the aqueous humor. In the initial phase of the process, a first incision of approximately parabolic shape is made in the sclera 3 to form a scleral flap 10 which is lifted upwards in the direction towards the cornea 4 to thereby expose a corresponding recess 11 which is bounded by a circumferentially extending side wall 11'. The scleral flap 10 is held in upwardly folded position by a tool or other means which are not shown for the sake of simplicity but are generally known by the artisan.

Figure 2:
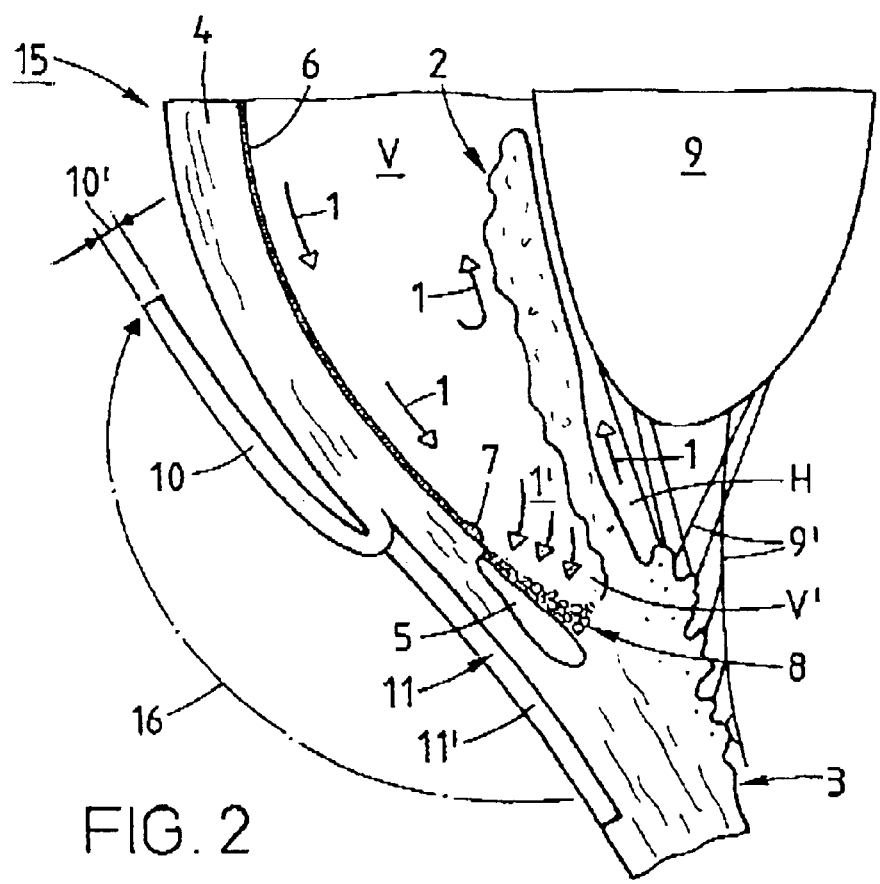
FIG. 2 is a schematic view of the portion of the eye of FIG. 1, taken along the line II—II in FIG. 1.

FIG. 2, which is a sectional view of the portion of the eye 15, taken along the line II—II in FIG. 1, shows a portion of the sclera 3, a portion of the cornea 4 with the Descemet's membrane 6 and the Schwalbe's line 7, a portion of the iris 2 and a portion of the lens 9 connected to the sclera 3 by means of the zonular fibers 9'. Further shown is the first scleral flap 10, which has been lifted upwards in the direction of arrow 16 and the corresponding recess 11, in addition to the Schlemm's canal 5 with the trabecular meshwork 8 disposed anteriorly thereof.

Arrows 1 and 1' in FIG. 2 designate essentially the circulation of aqueous humor and the natural drainage thereof. Aqueous humor, which in a healthy eye, regenerates continually, flows according to arrow 1 from the posterior chamber H to the anterior chamber V and is conducted at the iridocorneal angle V' (angulus irido-cornealis) in the direction of arrow 1' via the trabecular meshwork 8 into the Schlemm's canal 5 and from there, via the natural channel system 3' (FIG. 1) to a natural venous system (not shown). When the trabecular meshwork 8 is partially or completely non-functional due to back-up or like blockage, the natural drainage of aqueous humor is limited to such an extent that the pressure inside the eye 15 rises to thereby restrict the blood circulation and thus the functionality of the optic nerve (not shown). The resulting disease is commonly known under the name "glaucoma" and may lead to blindness of the affected eye.

Before incising the sclera 3 in a manner shown in FIG. 1, a micro-surgical procedure is carried by which the conjunctiva (not shown) is retracted with a suitable tool for exposing a sufficient portion of the sclera 3. After the first incision, the formed scleral flap 10 is folded upwards in the direction towards the cornea 4, thereby exposing the first recess 11 with its circumferential side wall 11'. The first incision may cover an area of, for example, 3 mm×3 mm with a depth which is so selected that the thickness 10' of the first scleral flap 10 is approximately ⅓ of the natural thickness of the sclera 3 in this zone, as depicted in FIG. 2. In this first phase, the Schlemm's canal 5 is not yet exposed.

Figure 3:
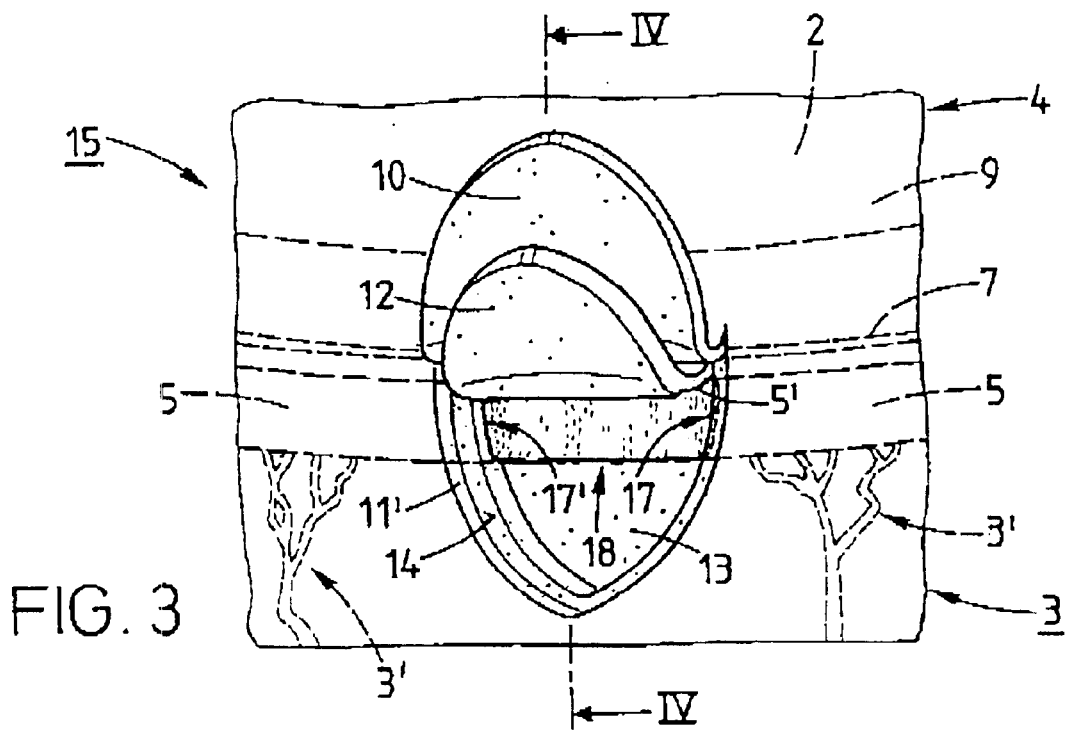
FIG. 3 is a schematic illustration of the portion of the eye of FIG. 1, showing a second parabolic incision within the area of first incision for formation of a second scleral flap which is folded upwards.

In a next step, as shown in FIG. 3, a second incision is made within the area of the first incision to form a second parabolic scleral flap 12 which is then lifted upwards in the direction of the cornea 4 in a direction of arrow 16' (FIG. 4), so that a second recess 13 is defined in correspondence with the second scleral flap 12 and bounded by a support surface 14. The depth of the second incision can, for example, be selected such that the Schlemm's canal 5 is exposed by a portion, denoted in its entirety by reference numeral 18. In this phase, two inlets 17 and 17' of the Schlemm's canal 5 in opposite disposition in the recess 13 are accessible for injection of an expanding medium by means of a probe, shown in FIG. 5.

Figure 4:
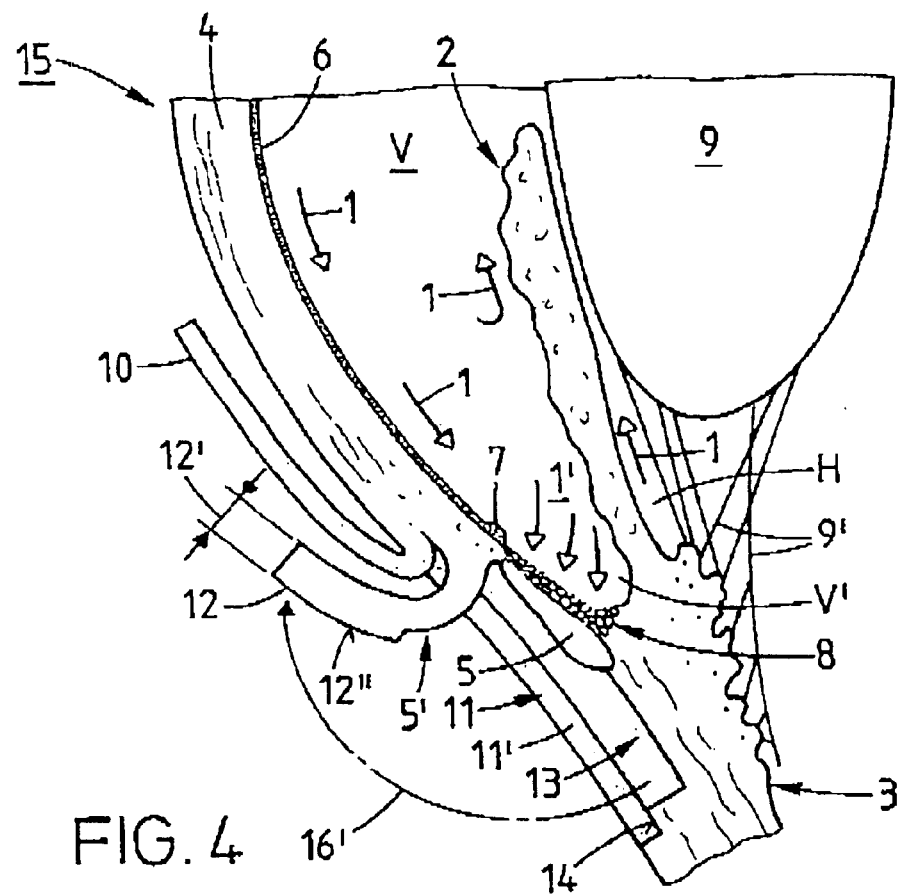
FIG. 4 is a schematic view of the portion of the eye of FIG. 3, illustrating both upwardly folded scleral flaps and taken along the line IV—IV in FIG. 3.

As shown in FIG. 3 and, in particular, in FIG. 4, the second scleral flap 12 is so formed that the Schlemm's canal 5 includes a depression 5' which exhibits a substantially grooved configuration and extends across the entire width of the second scleral flap 12.

FIG. 4 shows the portion of eye 15, taken along the line IV—IV in FIG. 3, with the two scleral flaps 10, 12 folded upwards in the direction of arrows 16, 16' and held in place by suitable means (not shown). The second incision results in a thickness 12' of the second scleral flap 12 that allows sufficient exposure and accessibility of the Schlemm's canal 5 via the inlets 17, 17' and the exposed portion 18. This is essentially realized by so selecting the depth of second incision that the groove-shaped depression 5' of the Schlemm's canal 5 remains at the inside 12" of the second scleral flap 12. FIGS. 3 and 4 also show the recesses 11, 13 in the sclera 3 with the side wall 11' and the support surface 14.

Figure 5:
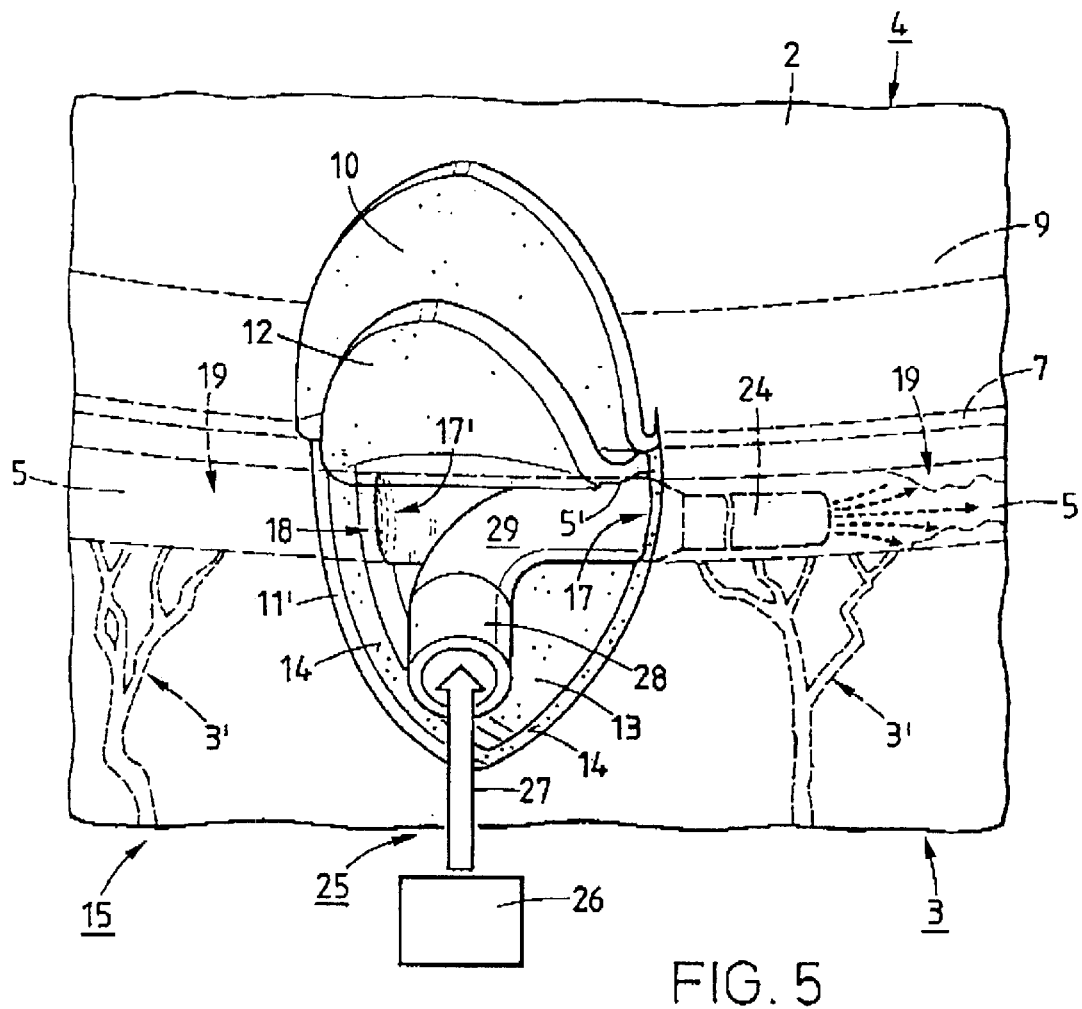
FIG. 5 is a schematic illustration of the portion of the eye of FIG. 3, depicting a probe for insertion into the exposed Schlemm's canal.
Figure 6:
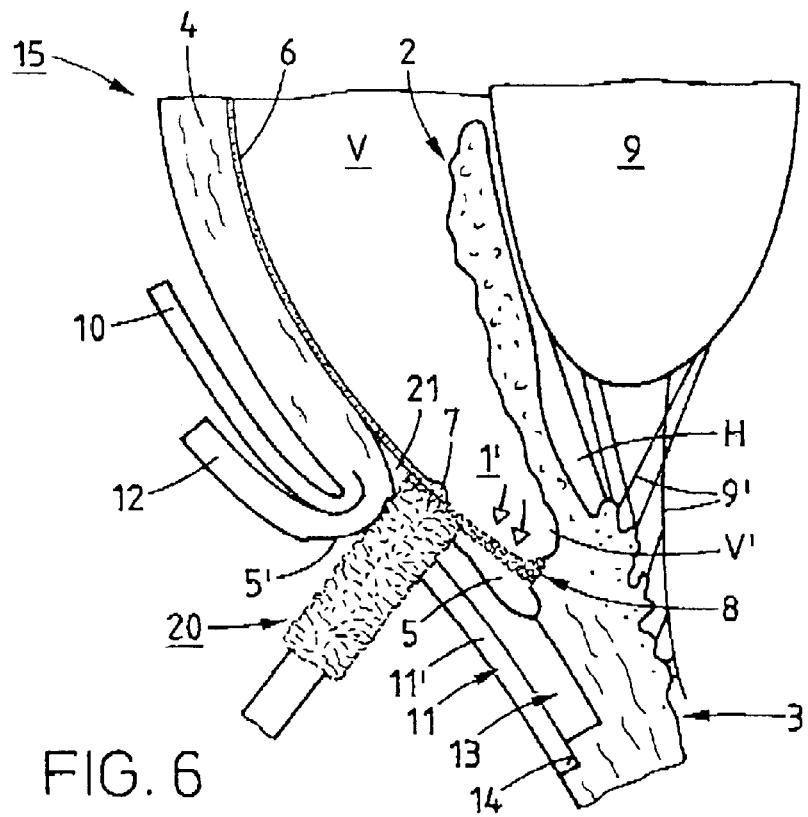
FIG. 6 is a schematic view of the portion of the eye of FIG. 4, illustrating the application of a swab for applying a small pressure force against the Schwalbe's Line in the area of the two upwardly folded scleral flaps.

FIG. 5, which is an enlarged illustration of the eye 15 of FIG. 3 and shows a portion of the sclera 3 and the two upwardly folded sclera flaps 10, 12 as well as the second recess 13 and the lateral support surface 14 of the sclera 3 with the channel system 3', depicts a next process phase, in which a suitable medium, preferably a high viscosity sodium hyaluronate solution is injected into the two lateral inlets 17 and 17' of the Schlemm's canal 5 by an injection unit, generally designated by reference numeral 25 to expand the lumen 19 of the Schlemm's canal 5. The injection unit 25 includes a probe 24 which, in the nonlimiting example of FIG. 5, is connected to an arcuate adapter 29 and inserted into one of the exposed inlets, here inlet 17, of the Schlemm's canal 5 for injecting the high viscosity sodium hyaluronate solution and expanding the lumen 19 of the Schlemm's canal 5 at least over the axial length of the inserted probe 24. After expanding the lumen 19 of the Schlemm's canal 5, the injection unit 25 with the probe 24 is withdrawn from the inlet 17 and can be turned for insertion in the opposite inlet 17' of the Schlemm's canal 5 for injection of the expanding medium and expansion of the lumen 19.

The injection unit 25 is connected via a supply conduit 28 to a pressure source 26, indicated schematically only, which may be formed by a single-chamber syringe or like device. The injected medium is forced into the lumen 19 of Schlemm's canal 5 in the direction of arrow 27, by means of the manually or electrically operated pressure source 26 via the supply conduit 28, adapter 29, and probe 24, for expansion of the lumen 19. After expansion of the Schlemm's canal 5, the injection unit 25 is removed. It will be appreciated by persons skilled in the art that operation and structure of such injection unit 25 are generally known by the artisan and do not form part of the present invention so that a detailed description thereof has been omitted for the sake of simplicity.

Figure 7:
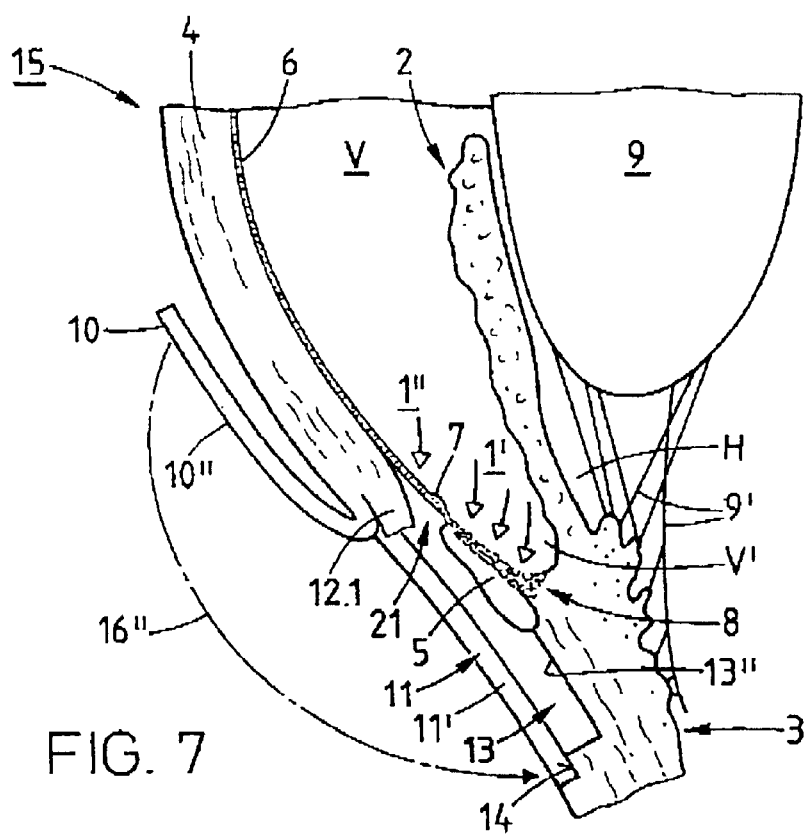
FIG. 7 is a schematic view of the portion of the eye of FIG. 6, illustrating a detachment of the Descemet's membrane from the cornea and the severed second scleral flap.

Turning now to FIG. 7, there is shown a further, optional, process step, after expansion of the Schlemm's canal 5 and withdrawal of the injection unit 25, representing a detachment of the Descemet's membrane 6 from the inner surface of the cornea 4 in the area of the Schwalbe's line 7. The detachment of the Descemet's membrane 6 is realized by using a swab 20 or like device to create an opening (window) 21 between the second scleral flap 12 and the Descemet's membrane 6, as shown schematically on an enlarged scale in FIG. 7. The opening 21 is substantially gap-shaped and extends in a manner not shown here across the entire width of the exposed portion 18 or second recess 13, as best seen in FIG. 8. The opening 21 provides a further connection between the anterior chamber V of the eye 15 and the second recess 13 so that aqueous humor can drain, apart from the natural outflow via the trabecular meshwork 8 in the direction of arrow 1', also via the substantially transparent Descemet's membrane 6, which is partly permeable for aqueous humor, in the direction of arrow 1", as shown in FIG. 7, and via the opening 21 to the recess 13 which is fluidly connected with the Schlemm's canal 5. The second recess 13, which essentially conforms to the scleral flap 12, forms a reservoir (FIG. 12) for aqueous humor which is drained from the reservoir-forming recess 13 through both lateral inlets 17, 17' into the Schlemm's canal 5, and from there via the channel system 3'.

The second scleral flap 12, save for a small remaining portion 12.1, is then, preferably, severed with a suitable surgical instrument (not shown), as shown in FIG. 8. It will be appreciated by persons skilled in the art, that the separation of the second sclera flap 12 may be carried out also before detachment of the Descemet's membrane 6 by means of the swab 20 to form the gap-shaped opening 21.

Referring now to FIG. 8, there is shown a schematic view of the eye 15, after severance of the second scleral flap 12, and illustration of the exposed portion 18 of the Schlemm's canal 5 and both confronting inlets 17, 17'. Implanted into the lumen 19 of the Schlemm's canal 5 on each of both sides of the exposed portion 18 are two support elements in spaced-apart side-by-side disposition. In the nonlimiting example of FIG. 8, two substantially ring-shaped support elements 30 are arranged on one side of the exposed portion 18, and two spherical support elements 33 are arranged on the other side of the exposed portion 18. FIG. 9 shows further exemplified support elements for implantation, that is a support element 45 in the form of a braided mesh is arranged on one side of the exposed portion 18, and a support element 50 in the form of a helical spring is arranged on the other side of the exposed portion 18.

FIG. 10A depicts a detailed perspective view, on an enlarged scale, of the support element 30. The support element 30 has a throughbore 32 and exhibits, preferably, an outer circular ring shape or elliptical ring shape. Suitably, the support element 30 is made of a material that will automatically conform to the lumen 19 of the Schlemm's canal 5. The support element 30 has a width 31 which is selected such that the support element 30 can be implanted in stable position in the lumen 19 and is prevented from toppling over in axial direction of the lumen 19.

FIG. 10B depicts a detailed view, on an enlarged scale, of the spherical support element 33. The support element 33 has at least one throughbore 34, preferably several bores 34 which are spaced in circumferential direction.

FIGS. 10C to 10E show further examples of support elements in accordance with the present invention. It will be appreciated by persons skilled in the art that the various configurations of support elements, described here, can be combined in any desired manner for implantation in the lumen 19 of the Schlemm's canal 5. Thus, the types of support elements implanted in FIGS. 8 and 9 are shown only for illustrative purposes.

FIG. 10C shows a support element 35 which is made from a flexible tube and has an outer configuration of circular ring shape or elliptic shape. The support element 35 is traversed in axial direction by a throughbore 36 which is in communication with a plurality of inlet openings 37 spaced in axial direction. With respect to the theoretic longitudinal axis X, the support element 35 is freely movable in its disposition and orientation, as shown schematically by broken lines, and thus can easily conform, as a consequence of its flexibility, to the inner configuration of the lumen 19 when inserted in the Schlemm's canal 5. The flexibility is however so limited that a kinking is eliminated.

FIG. 10D shows a support element 40 which is also made from an elongate flexible tube 41 and is traversed in axial direction by a throughbore 41' which is communication with a plurality of apertures 42, 42' spaced from one another in axial direction. The support element 40 has further arranged, preferably formed, thereon, a plurality of protrusions 43, 43', 43" which are spaced from one another in axial direction. The apertures 42, 42', which communicate with the throughbore 41', are preferably arranged in diametrically confronting disposition on the longer side of the support element 40. As shown in FIG. 10E, the support element 40 has an outer elliptic configuration which substantially conforms to the configuration of the Schlemm's canal 5. This type of support element 40 is used, primarily, for implantation in the exposed portion 18 of the Schlemm's canal 5 in the area of the second scleral recess 13 of the sclera 3. The function of the support element 40 will be described in more detail with reference to FIGS. 11 and 12.

FIG. 10F shows in more detail the support element 45 in the form of a braided mesh. The support element 45 is made from a plurality of threads 46 (filaments) which are helically intertwined to form the braided mesh, which has spacings 47, 47', 47" formed between the threads 46 for drainage of aqueous humor. Like the support element 35, the support element 45 is capable to conform by itself to the outer configuration of the lumen 19 of the Schlemm's canal 5.

FIG. 10G shows in more detail the support element 50, which, for example, is formed from a single, helically twined thread 51 (filament). Aqueous humor is drained between spacings 52, 52' of the individual windings of the support element 50. Like the support element 35, the support element 50 is capable to conform by itself to the outer configuration of the lumen 19 of the Schlemm's canal 5.

The elongate support elements 35, 40, 45 or 50, as shown in FIGS. 10C, 10F and 10G may be implanted in the portion 18 of the Schlemm's canal 5, exposed in the area of the second recess 13 of the sclera 3, as well as in the lumen 19 of the Schlemm's canal 5. Implantation of the elongate support element 35, 45, 50 in the exposed portion of the Schlemm's canal 5 is also feasible, as will be described in more detail with reference with FIGS. 13 and 14.

FIG. 11 shows implantation of spaced apart, ring-shaped support elements 30 on both sides of the second recess 13 in the lumen 19 of the Schlemm's canal 5, whereas a support element 40 is placed in the area of the second recess 13 of the sclera 3 in the exposed portion 18 of the Schlemm's canal 5. The support element 40 is so disposed in the exposed portion 18 of the Schlemm's canal 5 that the residual portion 12.1, which has been left from the second scleral flap 12 and extends across the entire width of the second recess 13, rests on the protrusions 43, 43', 43" of the support element 40.

After severance of the second scleral flap 12 and implantation of selected ones of the support elements, the first sclera flap 10 is folded back and, as shown in FIG. 12, placed on the parabolic support surface 14. Subsequently, the first scleral flap 10 is sutured partially, in a manner known per se, to the sclera 3. As the second sclera flap 12 has been separated, a subscleral space 13' is created in the form of the flat recess 13 behind the first scleral flap 10 and preferably filled by means of a syringe (not shown) with high viscosity medium, such as sodium hyaluronate, before completely rejoining the first scleral flap 10. This prevents an inside surface 10" of the repositioned first scleral flap 10 to come into contact with the inside surface 13" of the recess 13, as shown in FIG. 12.

FIG. 12 shows the implanted support element 40 according to FIG. 11 along the section line XII—XII on an enlarged scale, with the scleral flap 10 being folded back, and the residual portion 12.1 of the second scleral flap 12, separated from the Descemet's membrane 6 and placed on the protrusions 43, 43', 43". The provision of the protrusions 43, 43', 43" prevents a closing of the gap-shaped opening 21 across the entire width of the exposed portion 18 of the Schlemm's canal 5.

As further shown in FIG. 12, the gap-shaped opening 21 provides an additional connection between the iridocorneal angle V' of the anterior chamber V and the second recess 13. Aqueous humor can thus drain in addition to the natural drainage in the direction of arrow 1' via the trabecular meshwork 8 also in the direction of arrow 1" via the substantially transparent and partially permeable Descemet's membrane 6 and via the gap-shaped opening 21 to the recess 13. The flat recess 13, which has a configuration that approximates the second scleral flap 12, forms the subscleral space 13' or a reservoir for aqueous humor, when the scleral flap 10 is folded back. From the subscleral space 13', aqueous humor is drained via the two inlets 17, 17', fluidly connected to the subscleral space 13', into the lumen 19 of the Schlemm's canal 5, and from there into the channel system 3'.

FIG. 13 shows implantation of spaced apart, ring-shaped support elements 30, according to FIG. 10A, on both sides of the second recess 13 in the lumen 19 of the Schlemm's canal 5. Instead of support elements 30, or in combination with the support elements 30, several spaced-apart spherical support elements 33 may be used for implantation in the lumen 19. There is also the option, as shown in FIG. 13, to implant the support element 45, according to FIG. 10F, in the exposed portion 18 of the Schlemm's canal 5.

FIG. 14 shows implantation of two spaced-apart, ring-shaped support elements 30, according to FIG.10A on one side in the lumen 19, whereas two spaced-apart, spherical support elements 33, according to FIG. 10B, are positioned on the other, opposite side in the lumen 19. This non-limiting example includes also the implantation of the support element 50 according to FIG. 10G in the exposed portion 18 of the Schlemm's canal 5.

Although not shown in the foregoing figures, there are other options available, for example to implant two or more ring-shaped support elements 30 or 33 on one side of the exposed portion 18 and one or more of the elongated support elements 35, 45, 50 on the opposite side into the lumen 19 of the Schlemm's canal 5. In addition, it may be suitable to implant the elongate support 40 according to FIGS. 10D and 10E in the exposed portion 18 of the Schlemm's canal 5.

Suitably, the support elements 30, 33, 35, 45, 50 are made from decomposable material, in particular material that is biolytically decomposable by the tissue of the Schlemm's canal 5 and/or the aqueous humor. Especially suitable are materials that biolytically decompose within 2 to 12 months after implantation. Examples for materials used for support elements 30, 33, 35, 45, 50 include a cross-linked sodium hyaluronate. There is, however, also the option, to make the support element, in particular the elongate support element 35, 40, 45, 50 that is implantable in the exposed portion 18 of the Schlemm's canal 5, from biocompatible material, e.g. plastic material, rust-free steel or special steel such as silver, gold or platinum.

While the invention has been illustrated and described as embodied in a method of and device for improving a drainage of aqueous humor within the eye, it is not intended to be limited to the details shown since various modifications and structural changes may be made without departing in any way from the spirit of the present invention.

What is claimed is:

1. A method for improving a drainage of aqueous humor in an eye of a living being by conducting the aqueous humor in the area of the irido-corneal angle of the anterior chamber via the trabecular meshwork to the Schlemm's canal and ultimately to the natural channel system, said method comprising the steps of:

incising a first lamellar section of the sclera to form a first scleral flap;

lifting the first scleral flap upwards in the direction of the cornea, thereby creating a recess in the sclera;

incising a second lamellar section in the area of the recess to thereby form a second scleral flap and a support surface bounding the scleral flap;

lifting the second scleral flap upwards in the direction of the first sclera flap, thereby creating a second recess and exposing a portion of the Schlemm's canal;

implanting in the lumen of the Schlemm's canal on each of both sides of the second recess, and, optionally, in the exposed portion of the Schlemm's canal, at least one support element, each said support element being made of a material that is decomposable by at least one of the components selected from the group consisting of tissue of the Schlemm's canal and aqueous humor;

folding the first scleral flap back, after severance of the second scleral flap, for placement upon the support surface, thereby confining a subscleral space adjacent the first scleral flap;

injecting a viscous medium into the subscleral space; and rejoining the first scleral flap to the sclera.

2. The method of claim 1 wherein said implanting step includes implanting on each of both sides of the exposed portion of the Schlemm's canal, at least two substantially ring-shaped support elements in spaced-apart disposition to hold the lumen of the Schlemm's canal in expanded position, with the support elements being made of biolytically decomposable material.

3. The method of claim 1 wherein said implanting step includes implanting on each of both sides of the exposed portion of the Schlemm's canal, at least two substantially spherically-shaped support elements in spaced-apart disposition to hold the lumen of the Schlemm's canal in expanded position, with the support elements being made of biolytically decomposable material.

4. The method of claim 1 wherein the support element has an elongate, tubular configuration to hold the lumen of the Schlemm's canal in expanded position, with the support element being made of biolytically decomposable material.

5. The method of claim 1 wherein the support element is a braided mesh of elongate configuration to hold the lumen of the Schlemm's canal in expanded position, with the braided mesh being made of a biolytically decomposable material.

6. The method of claim 1 wherein the support element being designed in the form of an elongate helical spring to hold the lumen of the Schlemm's canal in expanded position, with the helical spring being made of a biolytically decomposable material.

7. The method of claim 1 wherein said implanting step includes implanting on each of both sides of the exposed portion of the Schlemm's canal, at least two substantially ring-shaped and/or spherical support elements in spaced-apart disposition in the lumen of the Schlemm's canal, and implanting in the exposed portion of the Schlemm's canal an elongate support element, to hold the lumen and the exposed portion of the Schlemm's canal in expanded position, with each of the support elements being made of biolytically decomposable material.

8. The method of claim 1, and further comprising the steps of detaching the second scleral flap along a portion thereof in the area of the Schwalbe's line from the partially aqueous humor permeable Descemet's membrane to form a gap-shaped opening; and holding the detached portion of the second scleral flap in open disposition by protrusions projecting out from the support element arranged in the exposed portion of the Schlemm's canal.

9. A device for improving a drainage of aqueous humor in an eye of a living being and maintaining a drainage of aqueous humor, comprising a support element for implantation into the lumen of the Schlemm's canal, said support element having a configuration selected from the group consisting of ring shape, spherical shape, elongate shape and tubular shape, wherein the support element is made of a biolytically decomposable material.

10. The device of claim 9 wherein material is decomposable by at least one of the components selected from the group consisting of tissue of the Schlemm's canal and aqueous humor.

11. The device of claim 9 wherein the support element has a throughbore defined by a cross section selected from the group consisting of circular ring shape and elliptical ring shape, with the material of the support element being deformable to conform to a cross section of the Schlemm's canal.

12. The device of claim 9 wherein the support element has a width, which exceeds a height of the substantially elliptical Schlemm's canal, for preventing a tilting of the implanted support element.

13. The device of claim 9 wherein the support element is a sphere having at least one throughbore.

14. The device of claim 9 wherein the support element is a sphere having a plurality of circumferentially spaced throughbores.

15. The device of claim 9 wherein the support element is a tube having a throughbore and defined by a cross section selected from the group consisting of circular ring shape and elliptical ring shape, said tube being formed with a plurality of spaced-apart apertures and being made of biolytically decomposable material which is flexible and freely movable in relation to a theoretical longitudinal axis to suit its disposition and orientation.

16. The device of claim 9 wherein the support element is an elliptic tube having a throughbore and defining a broad side and a narrow side, said broad side of the tube formed with a plurality of apertures which are spaced from one another in axial direction, and said narrow side of the tube being formed with at least two protrusions spaced from one another in axial direction and projecting radially outwards.

17. The device of claim 9 wherein the support element of elongate configuration is made as a braided mesh which is freely movable to suit its disposition and orientation.

18. The device of claim 9 wherein the support element is configured as a flexible helical spring of elongate configuration and is freely movable to suit its disposition and orientation.

19. The device of claim 9 wherein the biolytically decomposable material is biolytically decomposable by at least one of the components selected from the group consisting of tissue of the Schlemm's canal and aqueous humor within a time period of 2 to 12 months after implantation.

20. The device of claim 19 wherein each support element is made of cross-linked sodium-hyaluronate.

* * * * *